(12) United States Patent
Zhu

(10) Patent No.: US 10,379,126 B2
(45) Date of Patent: Aug. 13, 2019

(54) SYSTEMS AND METHODS FOR PROTEOMIC ANALYSIS

(71) Applicant: THE REGENTS OF THE UNIVERSITY OF MICHIGAN, Ann Arbor, MI (US)

(72) Inventor: Haojie Zhu, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 253 days.

(21) Appl. No.: 15/334,902

(22) Filed: Oct. 26, 2016

(65) Prior Publication Data

US 2017/0122962 A1 May 4, 2017

Related U.S. Application Data

(60) Provisional application No. 62/247,524, filed on Oct. 28, 2015.

(51) Int. Cl.
*G01N 33/68* (2006.01)
*C12N 9/14* (2006.01)
*B65D 19/44* (2006.01)
*B65D 19/00* (2006.01)

(52) U.S. Cl.
CPC ..... *G01N 33/6848* (2013.01); *G01N 33/6827* (2013.01); *B65D 19/0038* (2013.01); *B65D 19/44* (2013.01); *B65D 2519/00024* (2013.01); *B65D 2519/00029* (2013.01); *B65D 2519/00034* (2013.01); *B65D 2519/00059* (2013.01); *B65D 2519/00064* (2013.01); *B65D 2519/00069* (2013.01); *B65D 2519/00268* (2013.01); *B65D 2519/00815* (2013.01); *B65D 2519/00835* (2013.01); *C12Y 304/00* (2013.01); *G01N 2570/00* (2013.01)

(58) Field of Classification Search
CPC ........... G01N 33/6848; G01N 33/6827; G01N 2570/00
See application file for complete search history.

(56) References Cited

PUBLICATIONS

Bantscheff et al. (Anal. Bioanal. Chem., 2012, 404:939-965) (Year: 2012).*
Geiger et al. (Nature Protocols, 2011, 6(2):147-157) (Year: 2011).*
Singh et al. (Journal of Proteome Research, 2008, 8:2201-2210) (Year: 2008).*
Pagel et al. (Expert Review of Proteomics, 2015, 12(3):235-253) (Year: 2015).*
Alves et al., "Assigning statistical significance to proteotypic peptides via database searches." J Proteomics. Feb. 1, 2011;74(2):199-211.
Arike et al., "Comparison and applications of label-free absolute proteome quantification methods on *Escherichia coli*." J Proteomics. Sep. 18, 2012;75(17):5437-48.

(Continued)

*Primary Examiner* — Jeremy C Flinders
(74) *Attorney, Agent, or Firm* — Casimir Jones, S.C.; Tanya Arenson

(57) ABSTRACT

Provided herein are compositions and methods for proteomic analysis. In particular, provided herein are compositions and methods for performing mass spectrometry-based protein quantitation analysis.

16 Claims, 11 Drawing Sheets

(56) References Cited

PUBLICATIONS

Beynon et al., "Multiplexed absolute quantification in proteomics using artificial QCAT proteins of concatenated signature peptides." Nat Methods. Aug. 2005;2(8):587-9.

Brun et al., "Isotope dilution strategies for absolute quantitative proteomics." J Proteomics. Jul. 21, 2009;72(5):740-9.

Brun et al., "Isotope-labeled protein standards: toward absolute quantitative proteomics." Mol Cell Proteomics. Dec. 2007;6(12):2139-49.

Chahrour et al., "Stable isotope labelling methods in mass spectrometry-based quantitative proteomics." J. Pharm Biomed Anal. Sep. 10, 2015;113:2-20.

Fallon et al., "Targeted quantitative proteomics for the analysis of 14 UGT1As and -2Bs in human liver using NanoUPLC-MS/MS with selected reaction monitoring." J Proteome Res. Oct. 4, 2013;12(10):4402-13.

Gerber et al., "Absolute quantification of proteins and phosphoproteins from cell lysates by tandem MS." Proc Natl Acad Sci U S A. Jun. 10, 2003;100(12):6940-5.

Hanke et al., "Absolute SILAC for accurate quantitation of proteins in complex mixtures down to the attomole level." J Proteome Res. Mar. 2008;7(3):1118-30.

Keshishian et al., "Quantification of cardiovascular biomarkers in patient plasma by targeted mass spectrometry and stable isotope dilution." Mol Cell Proteomics. Oct. 2009;8(10):2339-49.

Mallick et al., "Computational prediction of proteotypic peptides for quantitative proteomics." Nat Biotechnol. Jan. 2007;25(1):125-31.

Mayr et al., "Absolute myoglobin quantitation in serum by combining two-dimensional liquid chromatography-electrospray ionization mass spectrometry and novel data analysis algorithms." J Proteome Res. Feb. 2006;5(2):414-21.

Pratt et al., "Multiplexed absolute quantification for proteomics using concatenated signature peptides encoded by QconCAT genes." Nat Protoc. 2006;1(2):1029-43.

Villanueva et al., "Isotope dilution mass spectrometry for absolute quantification in proteomics: concepts and strategies." J Proteomics. Jan. 16, 2014;96:184-99.

\* cited by examiner

SYSTEMS AND METHODS FOR PROTEOMIC ANALYSIS

The present application claims priority to U.S. Provisional Patent Application 62/247,524, filed Oct. 28, 2015, which is herein incorporated by reference in its entirety.

STATEMENT REGARDING FEDERALLY SPONSORED RESEARCH OR DEVELOPMENT

This invention was made with government support under W911NF-10-1-0518 awarded by the U.S. Army Research Laboratory's Army Research Office (ARO). The Government has certain rights in the invention

FIELD OF THE DISCLOSURE

Provided herein are compositions and methods for proteomic analysis. In particular, provided herein are compositions and methods for performing mass spectrometry-based protein quantitation analysis.

BACKGROUND

Mass spectrometry (MS)-based absolute targeted protein quantification is being increasingly adopted in proteomics research, and has proven its utility in both basic research and clinical biomarker discovery and validation. Several approaches have been developed to determine absolute quantity of targeted proteins in various biological samples based on the use of different stable isotype-labeled internal standards (IS), such as synthetic peptides (AQUA) (Gerber et al., *Proc Natl Acad Sci USA* 2003, 100, (12), 6940-5; Keshishian et al., *Mol Cell Proteomics* 2009, 8, (10), 2339-49) quantification concatemers (QconCATs) (Beynon et al., *Nat Methods* 2005, 2, (8), 587-9; Pratt et al., *Nat Protoc* 2006, 1, (2), 1029-43) and full-length protein standards (PSAQ) (Hanke et al., *J Proteome Res* 2008, 7, (3), 1118-30; Brun et al., *Mol Cell Proteomics* 2007, 6, (12), 2139-49). A combination of these approaches with modern MS/MS technologies, mainly multiple reaction monitoring (MRM), permits high accuracy and precision in absolute protein quantification.

To perform AQUA, the most commonly used absolute protein quantification method, isotopically labeled synthetic peptides are added to digested protein samples as the IS, followed by peptide extraction and MS analysis. Protein quantity is determined according to the peak ratios of unlabeled natural peptides to their heavy labeled counterparts. AQUA is based on the assumptions that 1) the targeted proteins are fully recovered after extraction; 2) the surrogate peptides are fully digested from targeted proteins in samples and remain intact during enzymatic digestion. However, these assumptions have never been fully verified for most proteins/peptides. Additionally, synthesis and purification of isotope labelling peptides can be expensive and time consuming.

A recent development of absolute protein quantification methods is the QconCATs (Beynon et al., supra; Pratt et al., supra). QconCATs are artificial proteins made of a number of concatenated surrogate peptides for various analyte proteins. Isotope-labeled QconCATs are obtained via the expression of artificial QconCATs genes in cells cultured in a heavy isotope enriched medium. QconCATs are added to protein samples before digestion, and the digested concatenated peptides serve as IS for quantification of different proteins. A major pitfall of this approach is that protein extraction and digestion efficiencies could vary significantly between QconCATs and native proteins due to different amino acid compositions.

Protein standards for absolute quantification (PSAQ) is an alternative approach of the AQUA and QconCATs. PSAQ involves biosynthesis and purification of stable isotope labeled analyte proteins and the addition of a known quantity of labeled proteins to samples (Hanke et al, supra; Brun et al., supra). PSAQ can overcome some drawbacks of AQUA, such as the variations associated with protein extraction and digestion. However, PSAQ is generally a low throughput assay, and each PSAQ protein standards has to be generated and purified individually, which is very labor intensive and expensive.

In addition to the stable isotope labelling-based methods, so-called "label-free" absolute quantification methods have been developed using unlabeled proteins as the external standard (Mayr et al., *J Proteome Res* 2006, 5, (2), 414-21; Arike et al., *J Proteomics* 2012, 75, (17), 5437-48). However, this approach is generally considered unfavorable in terms of accuracy and precision when compared with the methods employing isotopically labeled IS.

Improved methods of protein quantitation are needed.

SUMMARY

Provided herein are compositions and methods for proteomic analysis. In particular, provided herein are compositions and methods for performing mass spectrometry-based protein quantitation analysis.

Embodiments of the present disclosure provide improved compositions and methods for targeted absolute quantitative proteomics with SILAC (stable isotope labelling by amino acids in cell culture) internal standards and unlabeled full-length protein calibrators (TAQSI). Embodiments of the present disclosure provide LC-MS/MS systems and methods for absolute quantification of targeted proteins with very high accuracy and precision. This approach offers several advantages, such as lower cost and improved robustness and accuracy, over current existing methods. This method was successfully applied (See e.g., experimental section) to absolute quantification of carboxylesterase 1 (CES1) expression in human livers.

For example, in some embodiments, the present disclosure provides a method of quantitating protein levels, comprising: a) obtaining a sample comprising i) a plurality of polypeptides; and ii) a plurality of full-length isotope-labeled polypeptides; b) extracting and digesting the sample to yield a prepared protein fraction; c) analyzing the prepared protein fraction with a liquid chromatography-mass spectrometry/mass spectrometry system to obtained mass spectrometry peak areas for the plurality of polypeptides and the full length isotope-labeled polypeptides; d) calculating relative peak areas of the plurality of polypeptides and the full length isotope-labeled polypeptides to obtained relative quantitative values; and e) comparing the relative peak area ratio of the polypeptides to a standard curve generated using protein quantitation standards to determine the absolute quantity of the plurality of polypeptides. In some embodiments, the sample is a cell lysate or a pool of a plurality of cell lysates from different samples or subjects. In some embodiments, the cell lysate is a human cell lysate. In some embodiments, the method further comprises the step of performing the method on two different samples and comparing the levels of the polypeptides in each of the two different samples. In some embodiments, the two different samples comprise a first sample from a healthy subject and a second sample from a subject with a disease (e.g., cancer or other disease). In some embodiments, the two different samples comprise a first sample from a subject administered a test compound and second sample from a subject not administered the test compound. In some embodiments, the sample is from a cell line or subject administered a test compound (e.g., drug). In some embodiments, the method further comprises the step of determining the identity of the polypeptides. In some embodiments, the full-length isotope polypeptides are obtained by culturing a cell in a medium containing stable heavy isotope-labeled amino acids. In some embodiments, the cell is the same type as the sample. In some embodiments, the heavy isotope medium comprises $^{13}$C and $^{15}$N. In some embodiments, the method quantifies as least 2 polypeptides (e.g., at least 5, 10, 15, 20, 50, 100, or more polypeptides). In some embodiments, the calculating and comparing is performed using a computer system (e.g., comprising a computer processor, computer software, and a display screen).

Further embodiments provide a kit or system, comprising: a) a plurality of full-length isotope-labeled polypeptides; and b) a plurality of matched protein quantitation standards. In some embodiments, the kit or system further comprises one or more of a LC-MS/MS device, a computer system, and one or more reagents (e.g., proteases, buffers, or urea).

Additional embodiments are described herein.

DEFINITIONS

Figure 1:
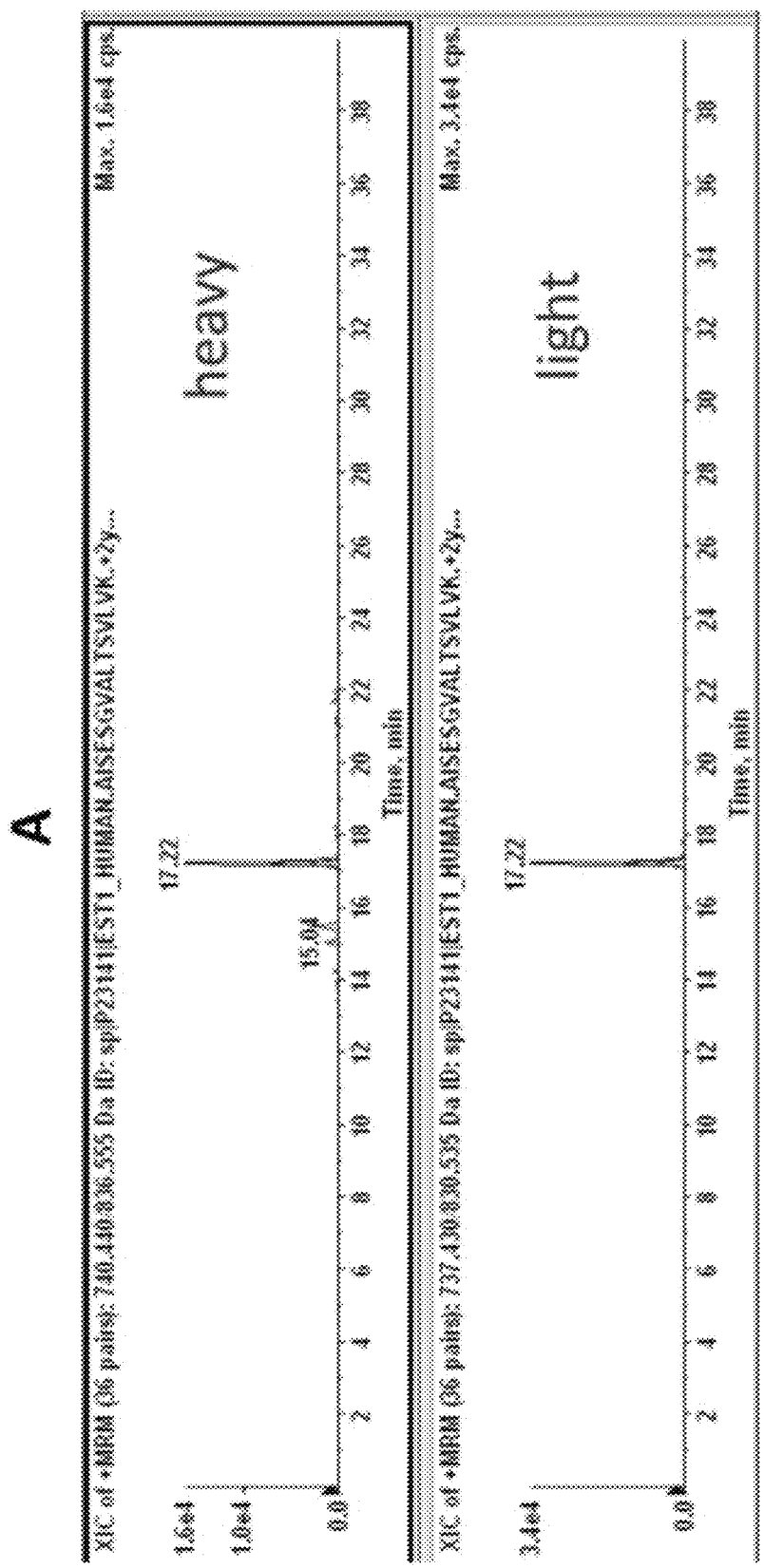
FIG. 1 shows representative LC-MS/MS chromatograms of the six selected unique CES1 peptides (A: AISES-GVALTSVLVK, B: FLSLDLQGDPR, C: TAMSLLWK, D: SYPLVC[CAM]IAK, E: ELIPEATEK, F: FWANFAR) and their corresponding isotope labeled peptides.
Figure 1:
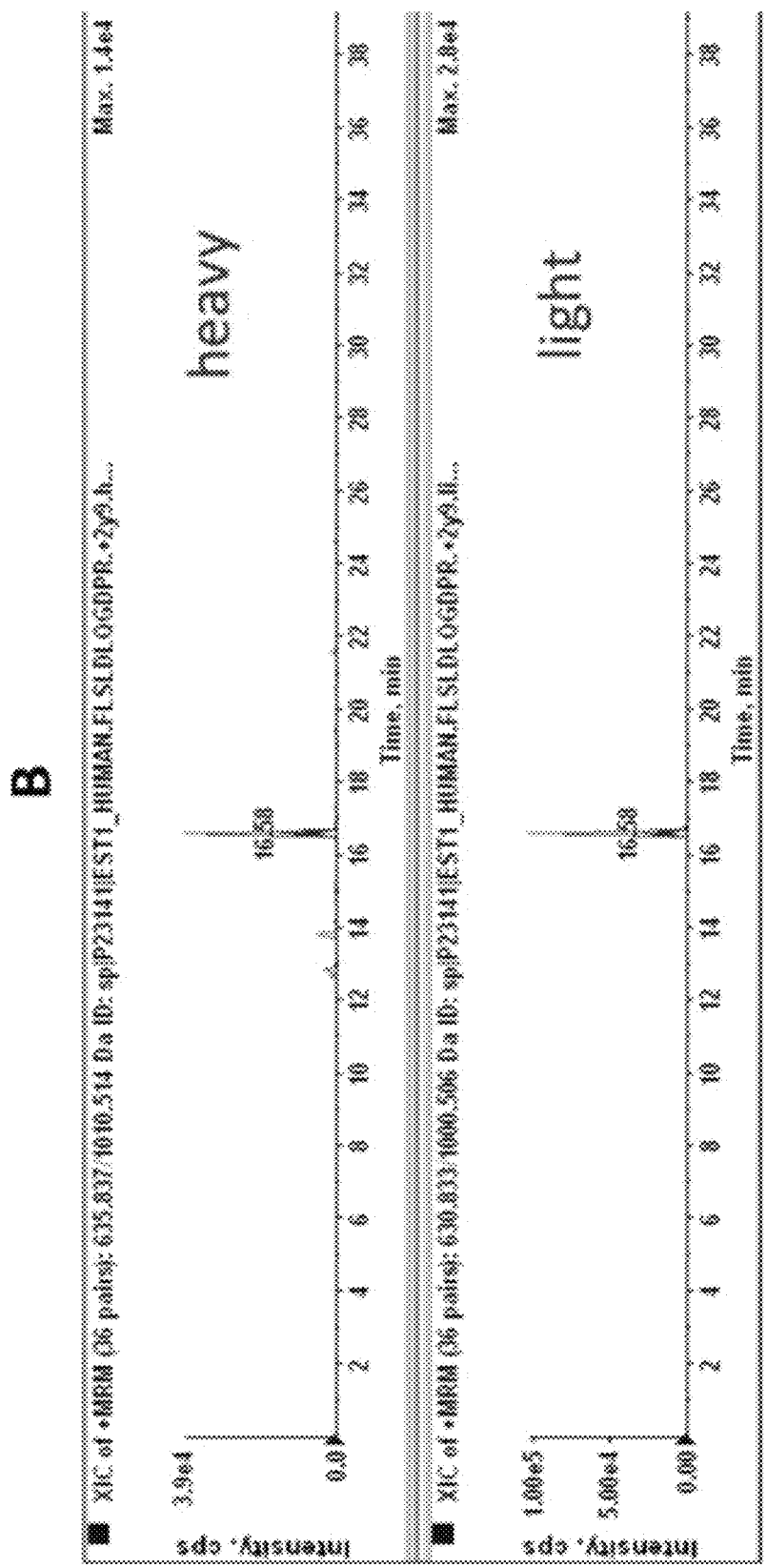
Figure 1:
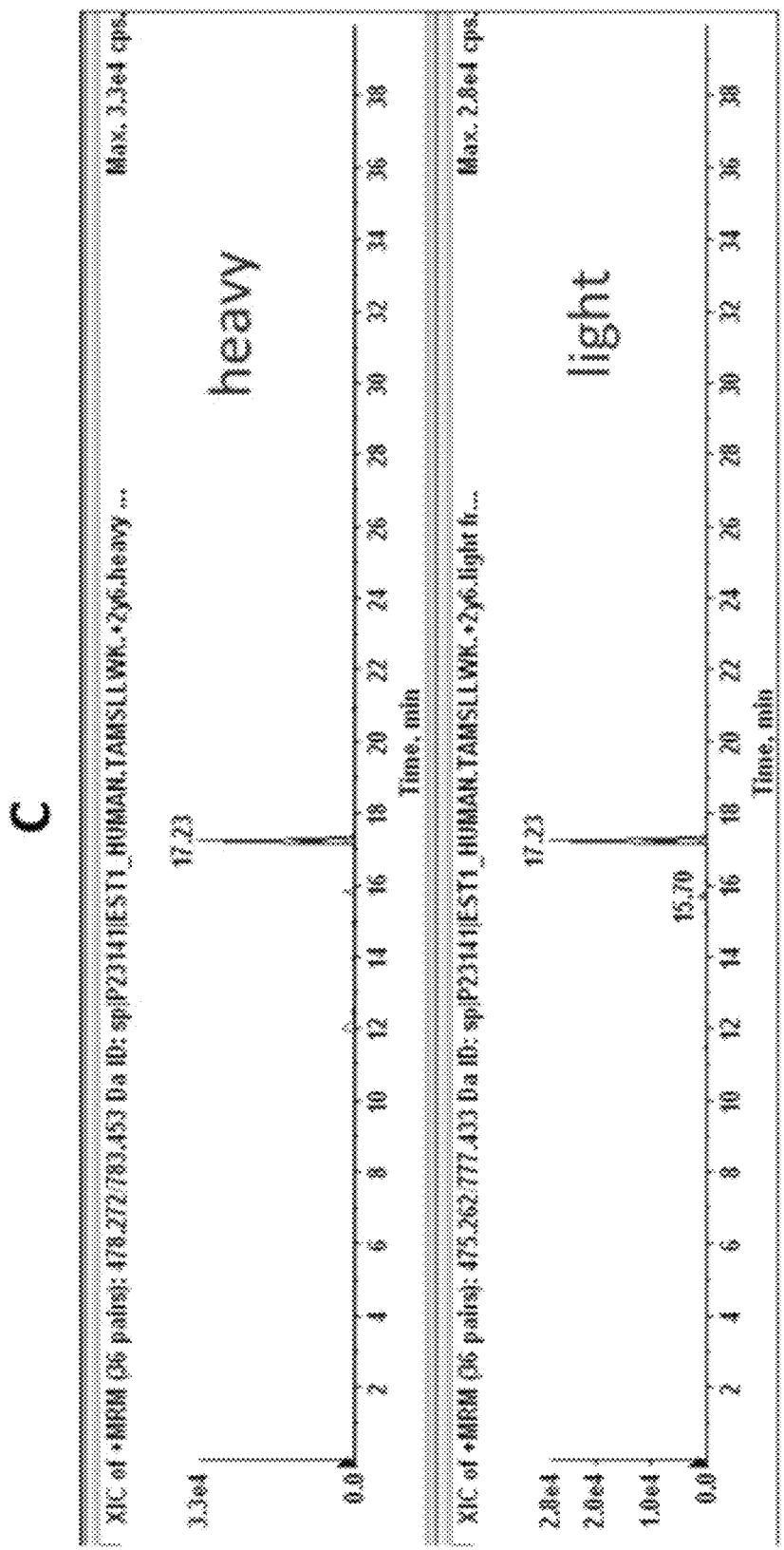
Figure 1:
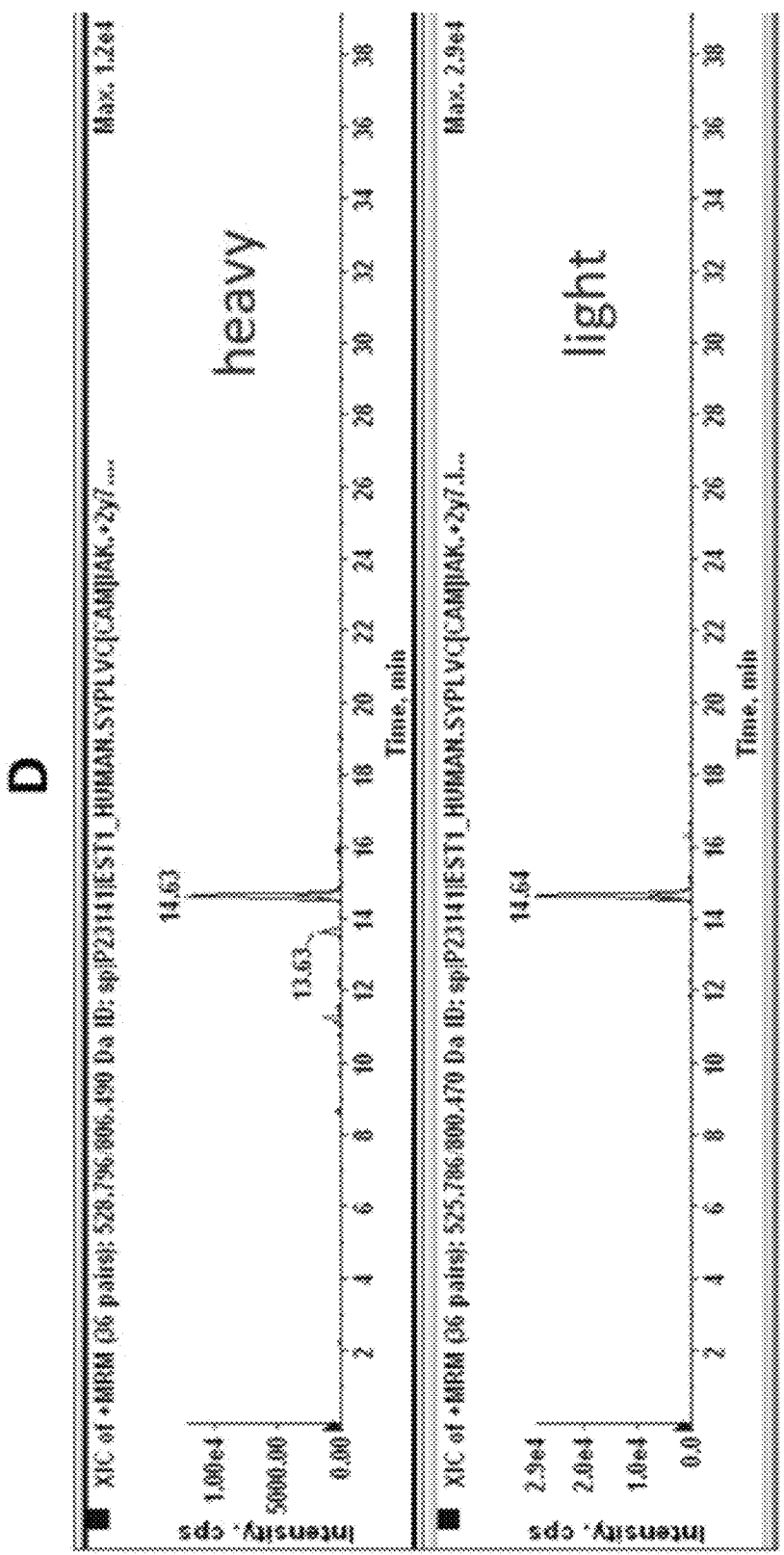
Figure 1:
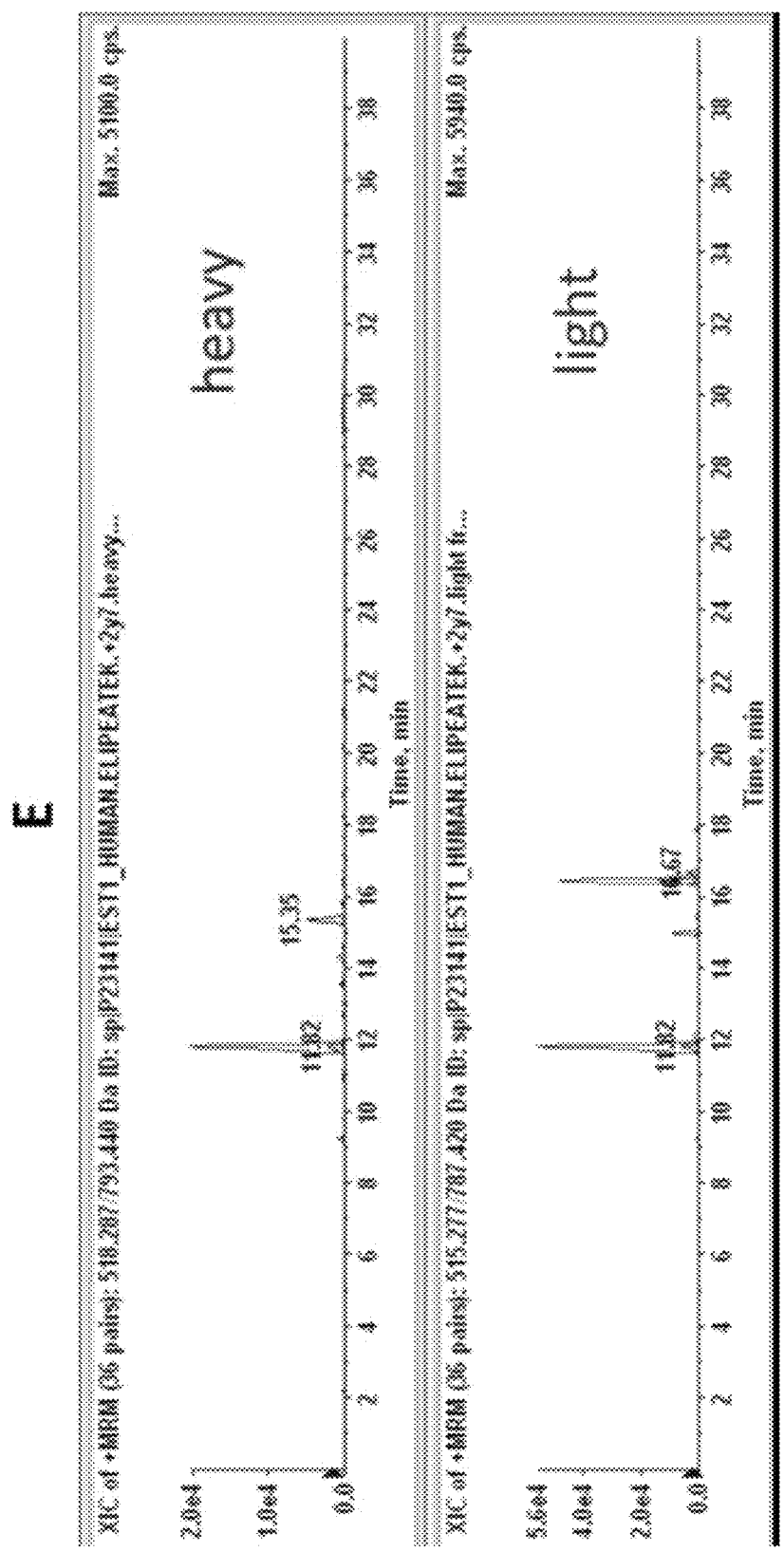
Figure 1:
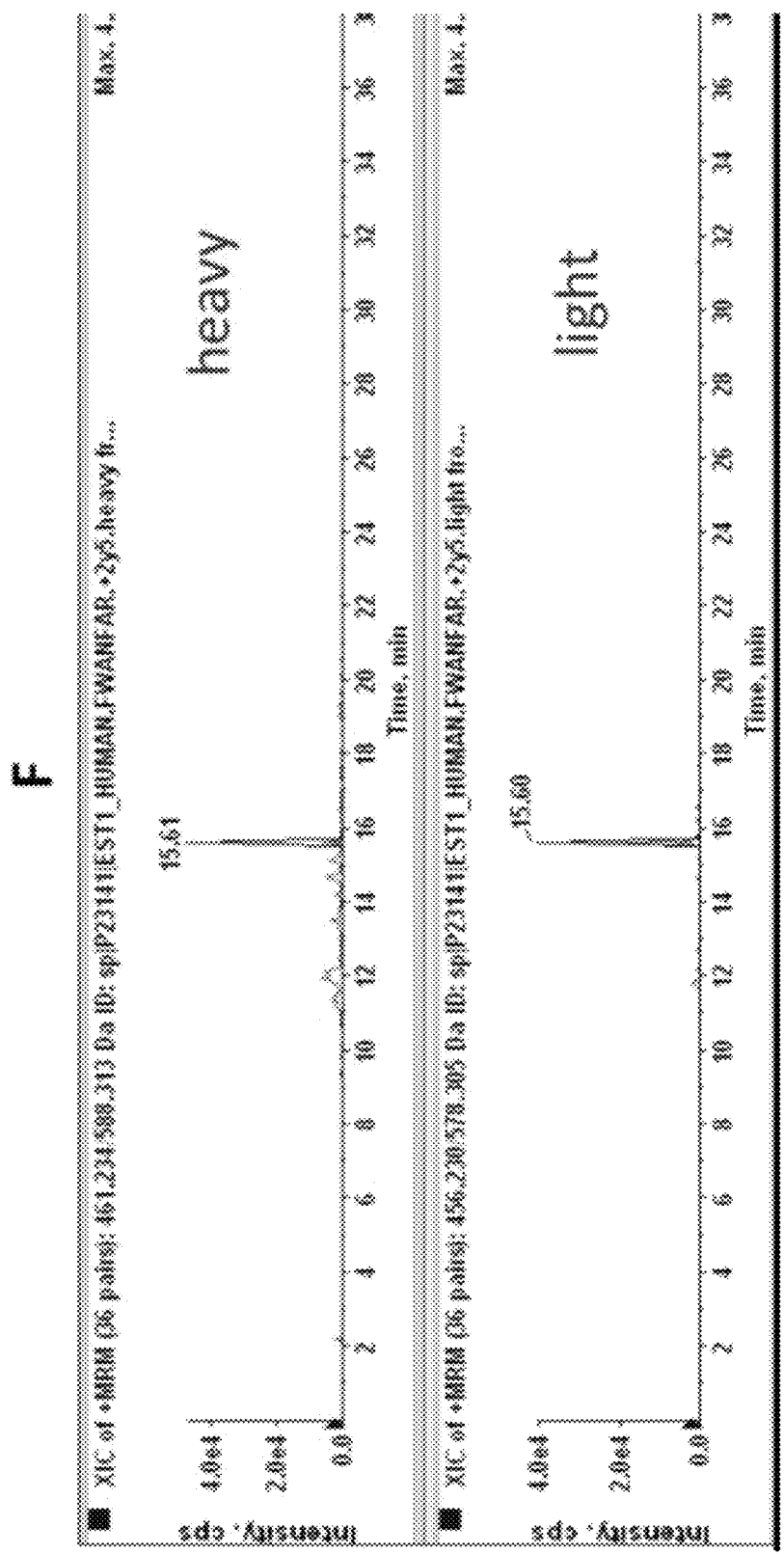

The expression "full-length isotope-labeled polypeptide" refers to a polypeptide whose chemical structure (e.g., primary structure), except for the presence of isotope, is either identical to the non-labeled polypeptide or closely related (e.g. isoforms or variants, in particular variants with at least 90% amino-acid identity or with at least 95% amino-acid identity).

As used herein, the term "detection system capable of detecting proteins" refers to any detection apparatus, assay, or system that detects proteins derived from a protein separating apparatus (e.g., proteins in one or fractions collected from a separating apparatus). Such detection systems may detect properties of the protein itself (e.g., UV spectroscopy) or may detect labels (e.g., fluorescent labels) or other detectable signals associated with the protein. The detection system converts the detected criteria (e.g., absorbance, fluorescence, luminescence etc.) of the protein into a signal that can be processed or stored electronically or through similar means (e.g., detected through the use of a photomultiplier tube or similar system).

As used herein, the terms "centralized control system" or "centralized control network" refer to information and equipment management systems (e.g., a computer processor and computer memory) operably linked to multiple devices or apparatus (e.g., automated sample handling devices and separating apparatus). In preferred embodiments, the centralized control network is configured to control the operations of the apparatus and/or device linked to the network. For example, in some embodiments, the centralized control network controls the operation of multiple chromatography apparatuses, the transfer of sample between the apparatuses, and the analysis and presentation of data.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refers to a device that is able to read a program from a computer memory (e.g., ROM or other computer memory) and perform a set of steps according to the program.

As used herein, the term "sample" is used in its broadest sense. In one sense it can refer to a cell lysate. In another sense, it is meant to include a specimen or culture obtained from any source, including biological and environmental samples. Biological samples may be obtained from animals (including humans) and encompass fluids, solids, tissues, and gases. Biological samples include blood products (e.g., plasma and serum), saliva, urine, and the like and includes substances from plants and microorganisms. Environmental samples include environmental material such as surface matter, soil, water, and industrial samples. These examples are not to be construed as limiting the sample types applicable to the present disclosure.

DETAILED DESCRIPTION

Provided herein are compositions and methods for proteomic analysis. In particular, provided herein are compositions and methods for performing mass spectrometry-based protein quantitation analysis.

The protein quantitation methods described herein overcome many of the disadvantages in existing mass spectrometry protein quantitation methods by providing absolute protein levels in a sample in a highly accurate and precise manner. As described herein, improved accuracy and precision in quantifying absolute protein levels are obtained by combining matched isotope labeled polypeptides and unlabeled calibration standards.

The widely used AQUA method is currently considered the golden standard for absolute protein quantification in both basic and clinical research (Chahrour et al., *J Pharm Biomed Anal* 2015; Brun et al., *J Proteomics* 2009, 72, (5), 740-9; Villanueva et al., *J Proteomics* 2014, 96, 184-99) To perform AQUA, isotope-labeled synthetic peptide(s) are added as IS to samples after protein digestion. Thus, isotope-labeled peptides are not able to correct for systematic and accidental errors that may have occurred during protein extraction and enzymatic digestion. It is also noted that proteotypic peptide yields are often proteins/peptides dependent, which makes it very difficult to establish a digestion protocol that is ideal for all targeted proteins. As shown in the FIG. 3 of the present specification, different digestion protocols can significantly affect the yields of targeted peptides. Furthermore, stability of peptides during digestion could introduce additional variability to the recovery of peptides. As a result, protein quantification could differ significantly when different isotope-labeled IS peptides or digestion protocols are utilized. For instance, the use of different isotope-labeled IS peptides resulted in more than 7-fold differences of UGT1A4 quantification in the same human liver sample (Fallon et al., *J Proteome Res* 2013, 12, (10), 4402-13).

Figure 3:
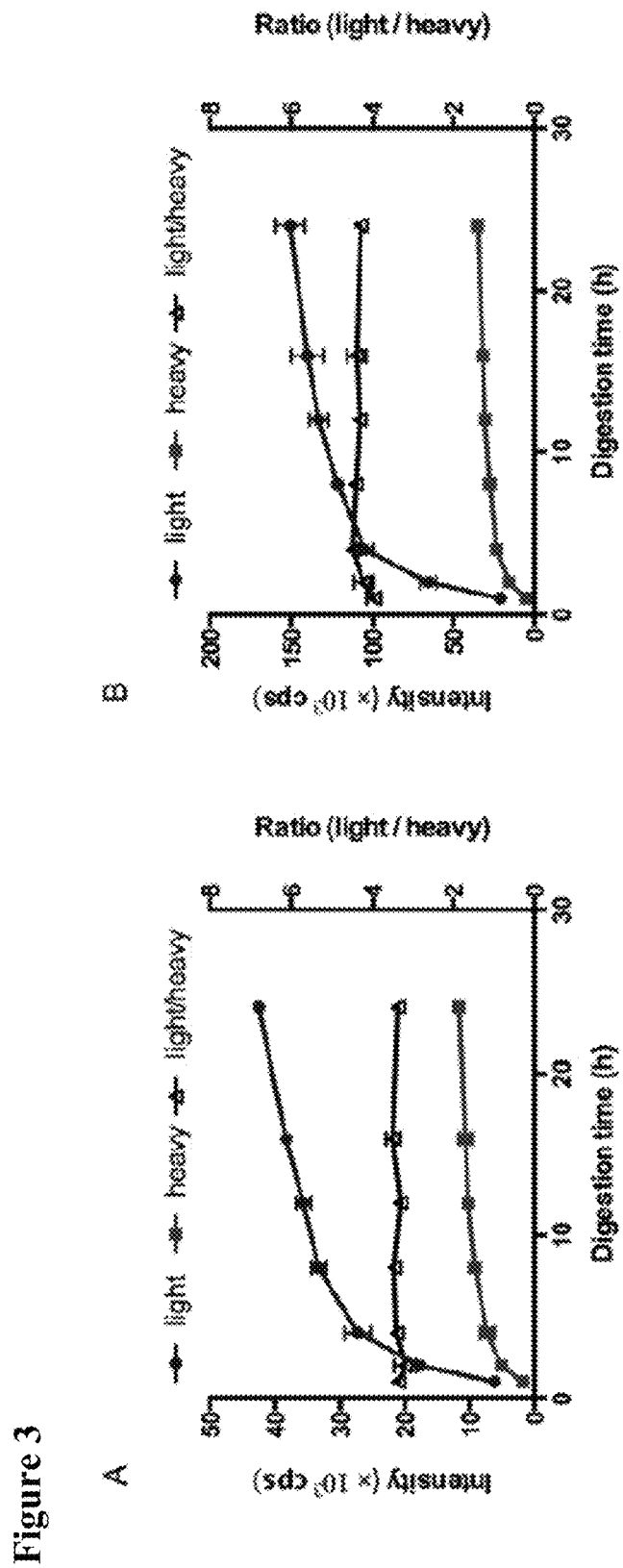
FIG. 3 (A-F) shows the impact of digestion incompletion on the MS/MS intensities of the six unlabeled and isotope-labeled CES1 signature peptides as well as their ratios.
Figure 3:
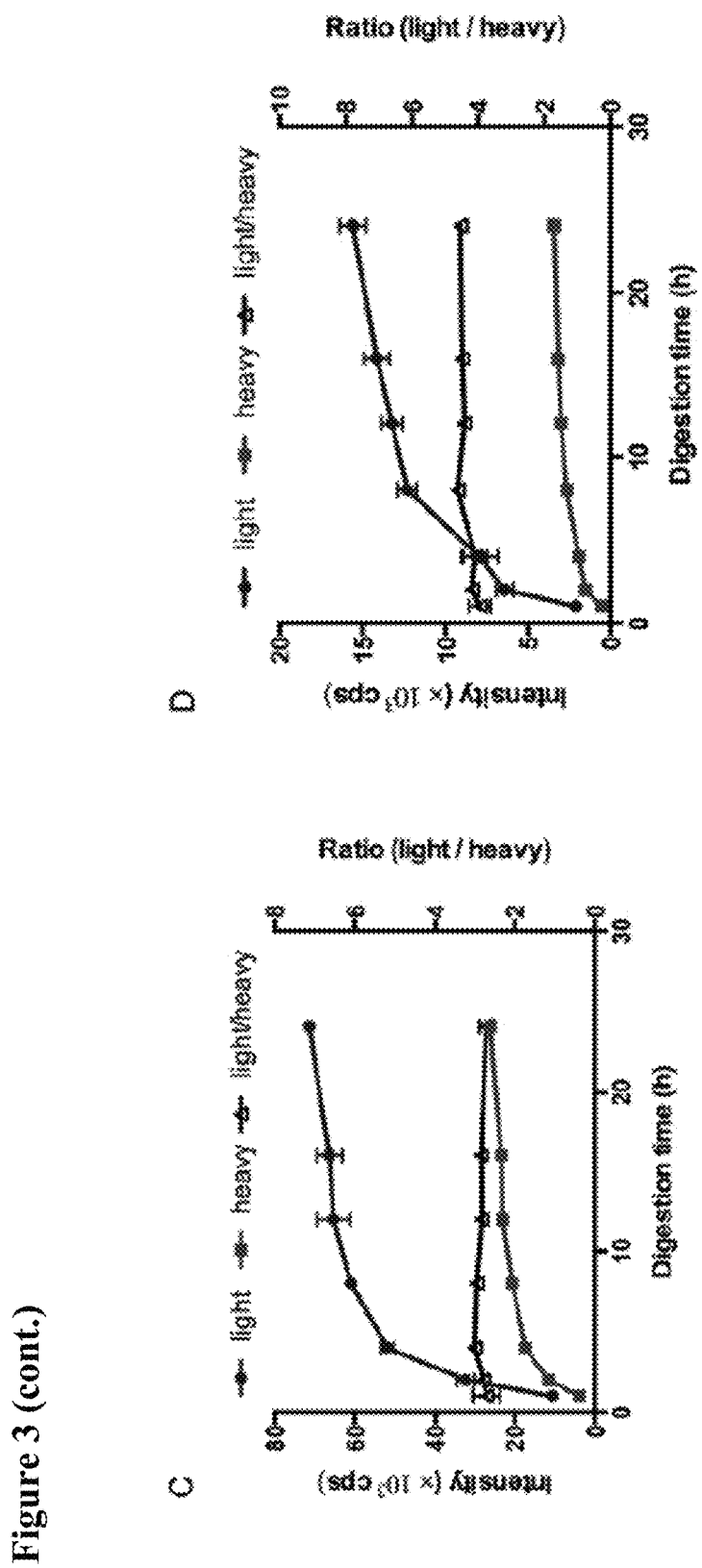
Figure 3:
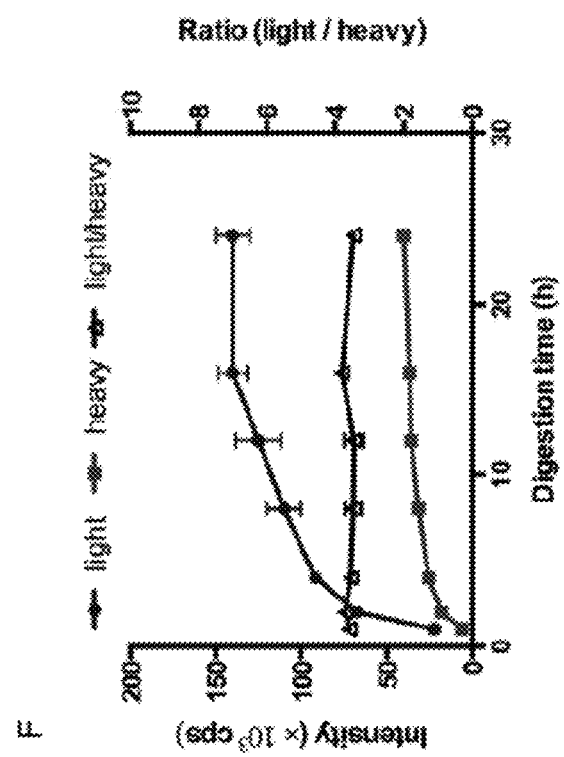
Figure 3:
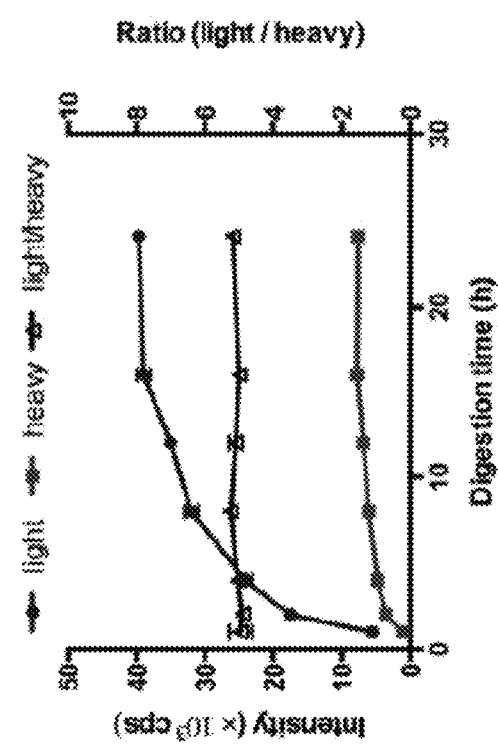

Distinct from AQUA in which synthetic isotope-labeled peptides IS are used, the TAQSI approach described herein employs full-length isotope-labeled native proteins obtained from SILAC as the IS. The full-length labeled proteins are added to lysate of tissues or cells before protein extraction and digestion. Therefore, all variabilities introduced from extraction and digestion processes as well as the downstream procedures are largely eliminated. Experiments described herein demonstrated that, even though the peptide recoveries varied during the time period of digestion, the unlabeled-to-labeled ratios of all six selected CES1 peptides remained consistent throughout the digestion process (FIG. 3). Thus, the TAQSI method is robust in terms of being resistant to the inter-assay variability caused by the selections of different surrogate peptides and digestion protocols.

Similar to the TAQSI approach, PSAQ assay can reduce the variability associated with protein digestion (Villanueva et al., supra). However, each PSAQ isotope standards need to be individually generated from cell free systems or SILAC and purified via customized assays before being able to serve as the standards for protein quantification. The whole procedure is often very expensive and time consuming. In contrast to PSAQ, the TAQSI method described herein utilizes unpurified multiple isotype-labeled IS proteins simultaneously generated from SILAC. Additionally, unlabeled full-length proteins, which serve as the external standards for the construction of calibration curves, are often commercially available, or can be readily prepared in house through standard molecular biological assays. Thus, the TAQSI method is more efficient and cost effective relative to the established PSAQ assay.

Figure 2:
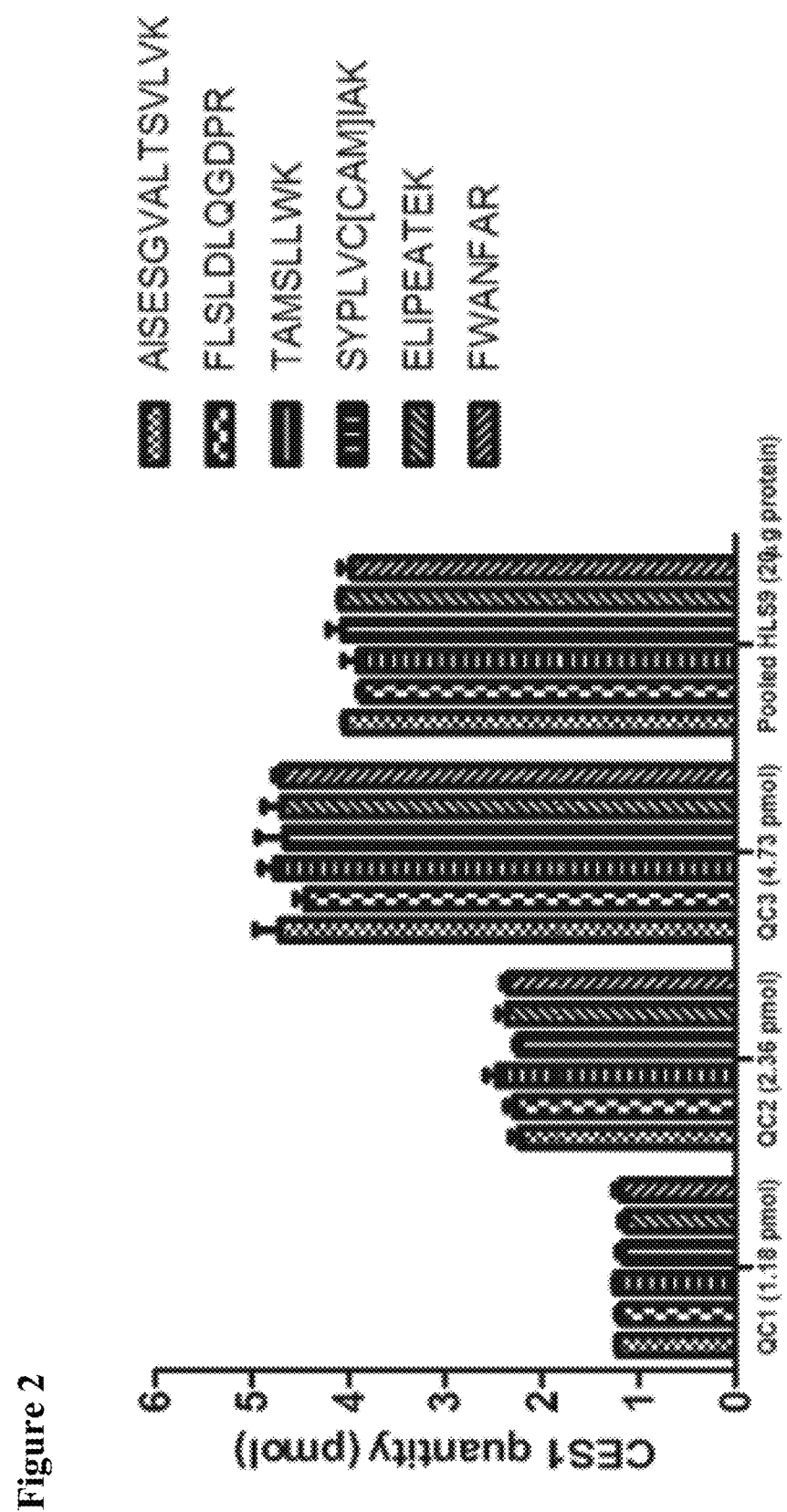
FIG. 2 shows absolute CES1 quantities in three quality controls (QCs) and pooled HLS9 samples determined using the six selected CES1 signature peptides. Nominal CES1 quantities in the low, medium, and high QC samples were 1.18, 2.36, 4.73 pmol, respectively.

Measurement errors of protein quantification can occur when samples contain nonsynonymous variants that reside in the selected signature peptide(s). As a general principle, peptides containing high-frequency nonsynonymous variants should be avoided when selecting surrogate peptides for protein quantification. However, the options of available peptides for protein quantification are often limited due to that the peptides also need to satisfy other criteria, such as specificity, MS/MS sensitivity, and digestion efficiency, etc. It is not uncommon that peptides with reported nonsynonymous variants are adopted as surrogate peptides for protein quantification. The TAQSI approach allows one to apply multiple signature peptides to protein quantification without increasing costs and assay complexity. The data described herein of absolute CES1 quantification demonstrated that very consistent quantifications are achieved across the different signature peptides (FIG. 2). Missing peaks of an unlabeled peptide indicate a homozygous nonsynonymous variant in the peptide whereas it would indicate the presence of a heterozygous nonsynonymous variant if the calculated protein quantity based on a selected peptide was approximately 50% of that determined from other signature peptides. Thus, cross examination of the data derived from different peptides not only enhances the confidence and reliability of the study but also allow one to identify the peptide(s) containing nonsynonymous variants and exclude it from the final data analysis.

The ideal signature peptides for protein quantification should meet several criteria including 1) be unique to targeted proteins; 2) generate good MS/MS responses; 3) chemically stable; and 4) unlikely to be affected by genetic variants. Some bioinformatics tools have been developed to aid in the selection of signature peptides (Mallick et al., *Nat Biotechnol* 2007, 25, (1), 125-31; Alves et al., *J Proteomics* 2011, 74, (2), 199-211). However, it remains a challenging task to predict the best performance peptides as the MS/MS profiles of peptides can be affected by many experimental conditions, such as MS instrument and sample preparation methods. AQUA assays usually do not test all candidate peptides due to the high costs of synthetic isotope-labeled peptides. Therefore, the peptide(s) selected from limited candidate peptides might not be the best performance peptides for AQUA protein quantification. The TAQSI method employs full-length unlabeled and labeled native proteins, which allows one to readily explore the performance of all digested peptides during method development. In the present example, a total of 22 CES1 candidate peptides were evaluated and six peptides with the best performance in terms of MS/MS responses and chromatographic selectivity were identified (FIG. 1).

The systems and methods described herein utilize the steps of obtaining full-length isotope labeled polypeptides of the polypeptides to be detected (e.g., by culturing cells in stable isotype-labeled medium such as SILAC), combining the isotope labeled polypeptides with one or more test samples, and digesting (e.g., with protease) and extracting the combined sample to yield a protein fraction for LC-MS/MS analysis. In some embodiments, calibration curves of known quantities of the polypeptides to be detected are further utilized (e.g., in a separate analysis reaction or combined with the test sample) for absolute quantitation.

Embodiments of the present disclosure utilize full-length isotope labeled polypeptides for relative quantitation in mass spectrometry analysis. Typically the isotope-labeled polypeptides may be labeled with isotopes of hydrogen, nitrogen, oxygen, carbon, or sulfur. Suitable isotopes include, but are not limited to: $^2$H, $^{13}$C, $^{15}$N, $^{17}$O, $^{18}$O, or $^{34}$S. For example the polypeptide may be uniformly labelled with $^{13}$C and/or $^{15}$N.

Metabolic isotope incorporation may be realized by in vivo expression such as growth of cells in SILAC medium (e.g., as described in Example 1). In some embodiments, isotope incorporation is realized by using cell-free extracts.

The present disclosure is not limited to particular proteases for the protein digestion step. As used herein, a "protease activity" is an activity which cleaves amide bonds in a polypeptide. The activity may be implemented by an enzyme such as a protease or by a chemical agent. Suitable proteases include, but are not limited to one or more of; serine proteases (e.g., such as trypsin, hepsin, SCCE, TADG12, TADG314); metalloproteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; cysteine proteases such as gingipains, and the like. Proteases may be isolated from cells or obtained through recombinant techniques. Chemical agents with a protease activity such as CNBr can also be used.

The present disclosure is not limited to particular sample types. While the disclosure is exemplified with human liver cells, any suitable sample can be analyzed using the systems and methods described herein.

Examples of samples on which the method according to the disclosure may be performed are biological fluids (blood, serum, plasma, cerebrospinal fluid, urine, saliva, lachrymal fluid, etc.), tissue and cells homogenates, cell culture supernatants, water, food, biocollection fluids and any biochemical fraction derived from the above materials. Biocollection fluids are fluids that are used for collecting particles which may be present in air or gas samples.

The methods described herein are suitable for multiplex quantitation of a plurality of polypeptides (e.g., 1, 5, 10, 15, 20, 500, 100, or more). In some embodiments, multiplex or non-multiplex sample preparation is automated (e.g., using automated sample handling apparatuses).

The present disclosure is not limited to the particular polypeptide(s) that are quantitated. Typically the target polypeptide is biomarker, a protein or a fragment thereof which is physiologically or pathologically present in biological fluids (e.g. proinsulin or insulin), a bacterial protein, a viral protein, a plant protein, a yeast protein, a mold protein, a fungal protein, an animal protein or a toxin, in particular a superantigenic toxin such as a staphylococcal superantigenic toxin. Typically the size of the target polypeptide may be larger than 5 kDa, 10 kDa, 50 kDa or 100 kDa.

In some embodiments, the polypeptides are biomarkers of drug efficacy or drug toxicity in humans, animals or in vitro models. Examples include, but are not limited to, biomarkers of hepatotoxicity, kidney toxicity, pulmonary toxicity, cardiotoxicity and/or neurological toxicity.

In some embodiments, polypeptides are therapeutic proteins. Examples include, but are not limited to, therapeutic antibodies, vaccinal antigens and immunotherapeutic allergen.

In some embodiments, polypeptides are diagnosis or prognosis biomarkers of one or more diseases. Examples include, but are not limited to, cardiovascular diseases, cancer diseases, metabolic diseases, neurological diseases, immunological diseases and infectious diseases.

In some embodiments, polypeptides are direct or indirect biomarkers of doping in athletes or animals such as horses. Examples include, but are not limited to, erythropoietin or an analogues thereof, antiangiogenic factors, growth hormone related polypeptides, insulin analogues and insulin-like growth factors.

In some embodiments, polypeptides are biomarkers of one or more pathogens. Examples include but are not limited to, pathogenic bacteria, such as bacteria belonging to the genus *Staphylococcus, Streptococcus, Salmonella, Bordetella, Escherichia, Listeria* or *Legionella*; pathogenic viruses such as HIV or Herpesvirus; parasites such as parasites belonging to the genus *Plasmodium* or *Taxoplasma*; pathogenic fungi such as fungi belonging to the genus *Cundida*; and prions.

In some embodiments, polypeptides are toxins. Examples include, but are not limited to, staphylococcal toxins, streptococcal toxins, shigatoxins, botulinum toxin and ricin.

In some embodiments, polypeptides are allergens. Examples include, but are not limited to, food allergens, plant allergens and insect sting allergens.

The present disclosure is not limited to particular liquid chromatography and mass spectrometry methods. Targeted and untargeted mass spectrometry approaches are suited to the method according to the disclosure. These approaches include but are not limited to: DDA (Data Dependent Analysis), AMT (Accurate Mass and Time Tag), SRM (Single Reaction Monitoring), MRM (Multiple Reaction Monitoring) and sMRM (scheduled MRM).

Any mass analyzer (e.g., time of flight, quadrupole, ion traps including linear quadrupole ion traps, ion cyclotron resonance and orbitraps) may be combined with any ionisation source (e.g., MALDI, ESI) and optionally any ion fragmentation method (e.g., in source fragmentation, collision induced dissociation, electron transfer dissociation, electron capture dissociation, infrared multiphoton dissociation, blackbody infrared radiative dissociation, surface induced dissociation).

Exemplary chromatography methods include, but are not limited to, HPLC, nanoLC (1D or 2D), gas chromatography, or capillary electrophoresis.

A further embodiment of the disclosure relates kits and/or systems comprising as separate parts isotope-labeled polypeptide(s) and quantification standards. In some embodiments, kits and/or systems further comprise one or more of reagents (e.g., proteases), LC-MS/MS systems, and computer systems.

In some embodiments, analysis of mass spectrometry data to generate protein quantification values is performed using a computer system. In some embodiments, computer systems comprise one or more of a computer process, computer software, and a display screen (e.g., monitor, tablet, smart phone, etc.)

The systems and methods described herein find use in variety of research, screening, clinical, biological, and chemical applications. In some embodiments, levels of polypeptides in different cell or sample types are compared (e.g., disease vs. healthy subjects; different populations of subject; and in drug screening and toxicity applications).

The method according to the disclosure may be used in a large variety of fields; such as, including but not limited to, proteomics, detection of biomarkers in biological samples, drug screening (e.g., functional assays of small molecule drugs) quality controls in the manufacture of vaccines and other bioproducts, biological and health hazard controls, food and water controls.

EXPERIMENTAL

The following examples serve to illustrate certain preferred embodiments and aspects of the present disclosure and are not to be construed as limiting the scope thereof.
Materials and Methods
Materials Urea, dl-dithiothreitol (DTT), trifluoroacetic acid (TFA), and acetonitrile were purchased from Fisher Scientific Co. (Pittsburgh, Pa.). Iodoacetamide (IAA) was the product of Acros Organics (Morris Plains, N.J.). TPCK-treated trypsin was obtained from Worthington Biochemical Corporation (Freehold, N.J.). Water Osis HLB columns were purchased from Waters Corporation (Milford, Mass.). Recombinant human CES1 (purity>95%) was the product of R&D system (Minneapolis, Minn.). Dulbecco's Modified Eagle Medium (DMEM), fetal bovine serum (FBS), and 100×antibiotics mixture containing penicillin (100 IU/ml) and streptomycin (100 μg/ml) were the products of Invitrogen (Carlsbad, Calif.). Trypsin-EDTA (0.25%) and SILAC Protein Quantitation Kit-DMEM containing SILAC DMEM (deficient in arginine and lysine), $^{13}C_6$ l-lysine-2HCl, $^{13}C_6$ $^{15}N_4$ l-arginine-HCl, and dialyzed FBS were obtained from Thermo Sientific (Waltham, Mass.). Sterile syringe filter with 0.2 μm sterile cellulose acetate membrane was purchased from VWR international Inc. (Bridgeport, N.J.). HepG2 cells were purchased from ATCC (HB-8065TM, Manassas, Va.). A total of 102 individual normal human liver samples were randomly selected from 535 banked samples. These liver samples were obtained from several sources including the University of Minnesota Liver Tissue Cell Distribution System, Cooperative Human Tissue Network (CHTN), and XenoTech LLC (Lenexa, Kans.). The donors consist of 92 Caucasians, 6 African-Americans, 2 Hispanics, and 2 classified as others, with 46 males and 56 females. Donor ages range from 22 to 81 years old.

Cell Culture and SILAC Labeling

The human hepatocellular carcinoma cell line HepG2, which exhibits similar gene expression pattern of human livers, was utilized to generate stable isotope labelling proteins. HepG2 cells were initially cultured in DMEM containing 10% FBS, 100 IU/ml penicillin and 100 µg/ml streptomycin at 37° C. under 5% $CO_2$ and 95% humidity.

SILAC culture medium consisted of SILAC DMEM supplemented with 1 mg/ml of $^{13}C_6$ l-lysine-2HCl and 1 mg/ml $^{13}C_6$ $^{15}N_4$ l-arginine-HCl, 10% dialyzed FBS, 100 IU/ml of penicillin and 100 µg/ml streptomycin. To obtain isotope-labeled cell culture, HepG2 cells were cultured in SILAC DMEM, and the medium were replaced every 3 days. Cells were subcultured when reaching 90% confluency. MS analysis showed that the incorporation rate of isotope-labeled arginine and lysine was more than 99% in cell S9 fractions after cells were cultured in SILAC medium for 5 generations or more. Thus, only the HepG2 cells with SILAC culture ≥5 passages were utilized in the study. To avoid potential variability in protein expression between different batches of cell culture, all SILAC S9 fractions were pooled, and subsequently used throughout the entire experiment.

Sample Preparation

Individual human liver S9 fractions (HLS9) were prepared from about 200 mg frozen liver tissues. The tissues were cut into small pieces (1×1×1 mm) and homogenized in 0.5 ml ice-cold phosphate buffer saline (PBS) using a microcentrifuge pestle (VWR International LLC, Chicago, Ill.) in 1.5 ml microcentrifuge tubes. The homogenates were centrifuged at 9000×g at 4° C. for 20 min. Following the centrifugation, the top layer containing fats was carefully removed, and the remaining samples were centrifuged again at 9000×g at 4° C. for 20 min to remove remaining fats. The resulting S9 fractions were collected and diluted to 2 mg/ml in PBS. HepG2 cell S9 fractions were prepared based on a previous method 9 Protein concentrations of human liver and HepG2 S9 fractions were determined using Pierce BCA protein quantification assay. An aliquot of 20 µl of HLS9 from each of the 102 samples were mixed to make the pooled HLS9 sample. The HLS9 samples were stored at −80° C. until use.

A 20 µg aliquot of HLS9 proteins was mixed with 40 µg proteins of SILAC HepG2 cell S9 fractions (IS) in Eppendorf Protein LoBind tubes. The proteins were precipitated by adding 10-fold volume of acetonitrile. The mixtures were briefly vortexed and then centrifuged at 17000×g for 10 min at 4° C. The supernatants were discarded, and the precipitated proteins were air dried for 5 min at room temperature. The dried proteins were re-suspended in 100 µl of freshly prepared 4 mM DTT/8 M urea solution, and incubated at 37° C. for 45 min. Following the incubation, samples were cooled to room temperature, and then alkylated by incubation with 100 µl of freshly prepared 20 mM IAA solution at room temperature for 30 min in dark. After alkylation, 800 µl water was added to dilute urea concentration to 0.8 M. Samples were then digested by trypsin at an enzyme/protein ratio of 1:500 in an incubation shaker at 200 rpm at 37° C. for 16 h. The tryptic digests were acidified by the addition of 1 µl TFA to terminate digestion. Digested peptides were extracted using Waters Oasis HLB columns according to the manufacture instruction. Extracted peptides were dried in Speed Vac SPD1010 (Thermo Scientific, Hudson, N.H.), and reconstituted in 80 µl of 50% acetonitrile. The reconstitutions were centrifuged at 17,000×g for 10 min at 4° C., and the supernatant was collected for LCMS/MS analysis.

Unlabeled recombinant full-length CES1 protein was utilized as the calibrators to establish the standard curves for quantification of CES1 expression in human livers. The CES1 calibrators were 0.59, 1.18, 2.36, 4.73 and 11.82 pmol, which cover normal range of CES1 expression in 20 µg proteins of human livers. Quality control (QC) samples were also prepared from the recombinant CES1 at 1.18, 2.36 and 4.73 pmol. Additionally, a pooled HLS9 sample (12 µg protein) was included in each run to further evaluate the between-run variability. Calibrators and QC samples were processed in parallel with liver samples using the aforementioned sample preparation protocol.

To evaluate the impact of digestion completion on protein quantification, CES1 was quantified after 1, 2, 4, 8, 12, 16, 24 h trypsin digestion using the same sample preparation method described above.

LC-MS/MS Analysis Workflow

The workflow of LC-MS/MS analysis of absolute CES1 expression was established with the assistance of the Skyline software (University of Washington, Seattle, Wash.). A list of 26 candidate peptides were generated based on the MS/MS spectrum currently available in NIST and human ISB Plasma spectral libraries (Table 1). The peptides that contain any nonsynonymous variants with minor allele frequencies >0.1% were excluded, which results in the removal of four peptides from the original list. A table containing the top three most intensive precursor-product ion transitions of each of the remaining 22 peptides and corresponding MS/MS instrumental parameters (e.g. dwell time, ionspray voltage, declustering potential, collision energy) was generated from Skyline software, and was integrated into the MS/MS method. The method was applied to the analysis of CES1 quantities in three pooled HLS9 samples. A total of 6 unique CES1 peptides that exhibited the highest intensity of MS/MS spectra were included in the final method (Table 2). No significant interference peaks were observed for the selected signature peptides (FIG. 1).

Digested bovine serum albumin (BSA) was utilized to generate the retention time predictor for the estimation of retention times of CES1 peptides. Standard curves were established based on the peak area ratios of the light (unlabeled) peptides from the recombinant CES1 to the heavy (isotope-labeled) peptides from the SILAC HepG2 S9 fractions. Assay accuracy and precision were assessed by analyzing four QC samples in each run.

Results

Consistency of Protein Quantification Between 6 Different Signature Peptides

Absolute CES1 quantities in three QCs and pooled human liver S9 samples were determined using the six selected CES1 signature peptides. Quantifications were consistent across the six peptides with the relative standard deviation (RSD) of 2.0%, 2.5%, 2.0%, and 2.3% for 1.18, 2.36, 4.73 pmol QCs, and pooled human liver S9, respectively (FIG. 2). The results indicate that any of the six surrogate peptides can be used to reliably quantify CES1 expression in human livers.

Linearity, Accuracy, and Precision

Calibration curves were established by plotting peptide quantity versus the peak area ratio of unlabeled-to-isotope labeled peptides, and were found to be highly linear within the tested range (0.59-11.82 pmol) for all peptides (Table 3). This range was anticipated to bracket possible CES1 quantities in 20 µg protein of human liver s9 fraction samples. The correlation coefficients of all six peptides were greater than 0.9999 under the experimental conditions described above. Precision and accuracy of the assay were determined utilizing three QC samples (1.18, 2.36, 4.73 pmol). As shown in Table 4, the inter- and intra-day precision measured as RSD were equal or less than 9.0% and 5.5%, respectively. The inter- and intra-day accuracy were within the ranges of 96.1%-102.2% and 94.6%-106.1%, respectively. Pooled HLS9 samples containing 20 µg total proteins were included in each run, serving as an additional QC. The between-run RSDs of the pooled HLS9 samples were between 0.7% and 4.4% for the six selected peptides.

Influence of Digestion Completion on Protein Quantitation

To evaluate the effect of digestion completion on CES1 protein quantitation, a mixture of 20 µg protein of pooled HLS9 samples and 40 µg protein of SILAC HepG2 cell S9 fractions (IS) were digested by trypsin at the enzyme/protein ratio of 1:500 for 1, 2, 4, 8, 12, 16, and 24 h. The intensity of MS/MS spectra of both the six unlabeled surrogate CES1 peptides and their corresponding isotope-labeled peptides were increased during the time of digestion from 0.5 to 8 h, and reached plateau after 8 h. However, the light to heavy peptide ratios that were used for CES1 quantitation remained consistent during the whole period time of digestion, indicating that incomplete digestion should not affect the method of protein quantitation (FIG. 3).

LC-MS/MS Quantification of CES1 Protein in Human Liver Samples

Figure 4:
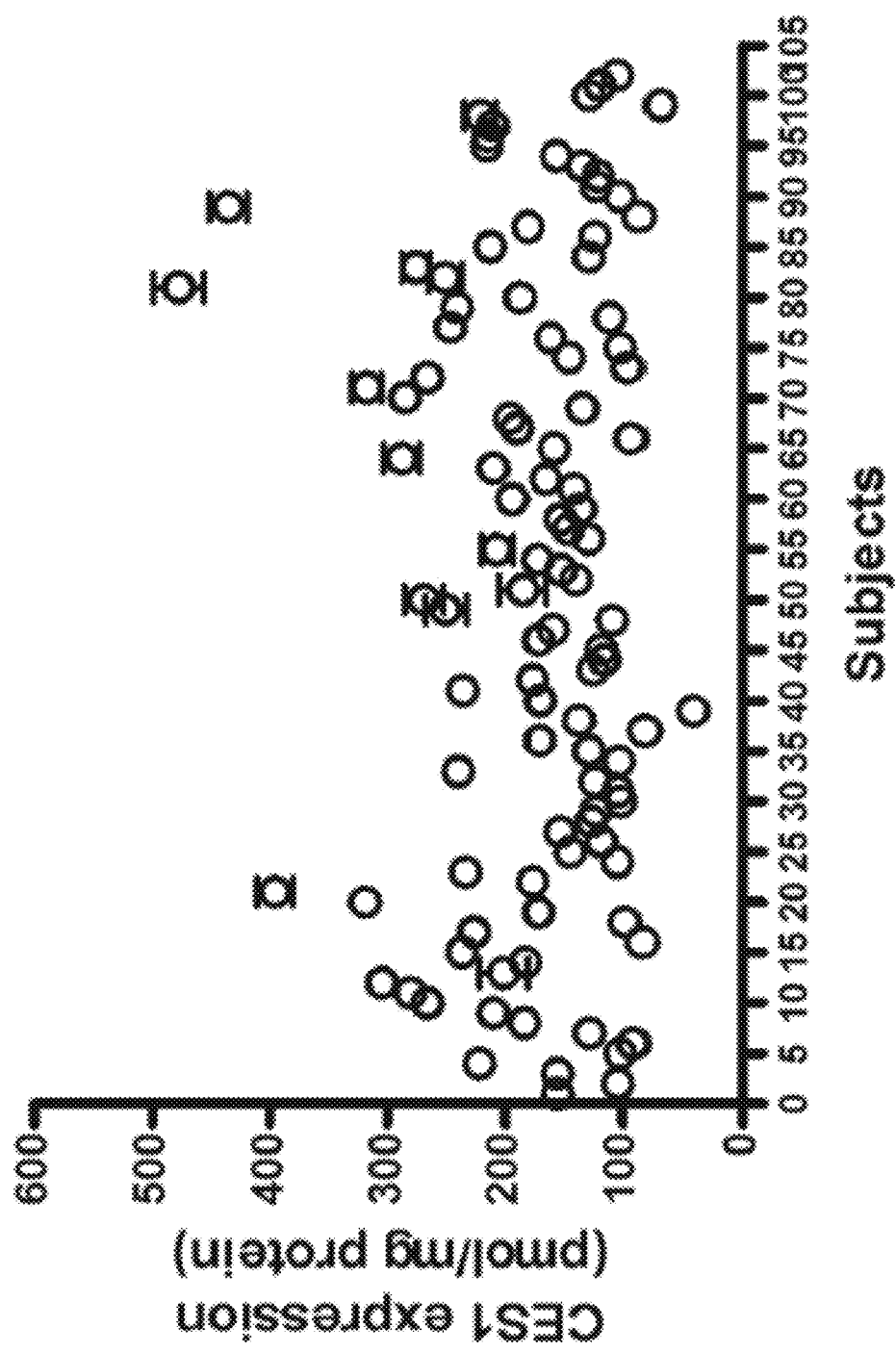
FIG. 4 shows absolute CES1 quantities (pmol/mg total protein) in 102 HLS9 samples.

CES1 expressions and activities vary significantly among individual human livers. The TAQSI protein quantification assay was applied to the determination of absolute CES1 expression in 102 individual human liver samples. CES1 expressions were found to range from 42.0±2.3 to 477.9±21.9 pmol/mg protein among those liver samples (FIG. 4). The mean expression level was 176.08±75.6 pmol/mg protein (10.0±4.2 µg/mg protein), which is about 1% of total proteins expressed in HLS9 samples.

In summary, this example describes a LC-MS/MS-based MRM absolute targeted protein quantification method named TAQSI. Relative to other existing methods, the TAQSI is highly accurate, precise, reproducible, and cost effective. This approach finds use, for example, in the study of protein expression in various biomedical research settings and absolute quantification of protein therapeutics in pharmaceutical industry. Additionally, high reproducibility of TAQSI makes it a preferred tool for the discovery and validation of clinical protein biomarkers. Clinical applications of the method include, for example, protein quantification-based diagnostics and protein biomarker-guided precision medicine.

TABLE 1

Candidate peptides for CES1 quantification

| Peptide sequences | CES1 nonsynonymous variants (MAF > 0.1%). |
|---|---|
| K.FVSLEGFAQPVAIFLGIPF AKPPLGPLR.F [36, 63] | |
| R.FTPPQPAEPWSFVK.N [64, 77] | rs2307240 (p.Ser76Asn) |
| K.AGQLLSELFINR.K [92, 103] | |
| K.LSEDCLYLNIYTPADLTK.K [111, 128] | |
| R.LGIWGFFSTGDEHSR.G [171, 185] | rs60054861 (p.Arg187Pro) rs60054861 (p.Arg187Gln) |
| R.GNWGHLDQVAALR.W [186, 198] | |
| R.AISESGVALTSVLVK.K [242, 256] | |
| K.GDVKPLAEQIAITAGCK.T [258, 274] | rs115629050 (p.Ala270Ser) |
| K.TTTSAVMVHCLR.Q [275, 286] | rs114119971 (p.His285Gln) |
| K.TEEELLETTLK.M [289, 299] | |
| K.FLSLDLQGDPR.E [301, 312] | |
| R.ESQPLLGTVIDGMLLLK.T [313, 329] | |
| K.TPEELQAER.N [330, 338] | |
| R.NFHTVPYMVGINK.Q [339, 351] | |
| K.QEFGWLIPMQLMSYPLSEG QLDQK.T [352, 375] | |
| K.TAMSLLWK.S [376, 383] | |
| K.SYPLVCIAK.E [384, 392] | |
| K.ELIPEATEK.Y [393, 401] | |
| K.YLGGTDDTVK.K [402, 411] | |
| K.DLFLDLIADVMFGVPSVIV AR.N [414, 434] | |
| R.DAGAPTYMYEFQYRPSFSS DMKPK.T [438, 461] | |
| K.TVIGDHGDELFSVFGAPFL K.E [462, 481] | |
| K.EGASEEEIR.L [482, 490] | |
| K.FWANFAR.N [498, 504] | |
| R.NGNPNGEGLPHWPEYNQK.E [505, 522] | |
| K.EGYLQIGANTQAAQK.L [523, 537] |

TABLE 2

MS/MS transitions and parameters of six unique surrogate peptides for CES1 quantification. The dwell time, ionspray voltage, and ion source temperature were 50 ms, 5500 v, and 500° C., respectively, for all peptides.

| Peptide ID | Q1 (Da) | Q3 (Da) | DP (V) | CE (eV) |
|---|---|---|---|---|
| AISESGVALTSVLVK. + 2y8.light | 737.43 | 830.535 | 84.9 | 37.8 |
| AISESGVALTSVLVK. + 2y6.light | 737.43 | 646.413 | 84.9 | 37.8 |
| AISESGVALTSVLVK. + 2y5.light | 737.43 | 545.366 | 84.9 | 37.8 |
| AISESGVALTSVLVK. + 2y8.heavy | 740.44 | 836.555 | 84.9 | 37.8 |
| AISESGVALTSVLVK. + 2y6.heavy | 740.44 | 652.434 | 84.9 | 37.8 |
| AISESGVALTSVLVK. + 2y5.heavy | 740.44 | 551.386 | 84.9 | 37.8 |
| FLSLDLQGDPR. + 2y9.light | 630.833 | 1000.506 | 77.1 | 31.7 |
| FLSLDLQGDPR. + 2y7.light | 630.833 | 800.39 | 77.1 | 31.7 |
| FLSLDLQGDPR. + 2y2.light | 630.833 | 272.172 | 77.1 | 31.7 |
| FLSLDLQGDPR. + 2y9.heavy | 635.837 | 1010.514 | 77.1 | 31.7 |
| FLSLDLQGDPR. + 2y7.heavy | 635.837 | 810.398 | 77.1 | 31.7 |
| FLSLDLQGDPR. + 2y2.heavy | 635.837 | 282.18 | 77.1 | 31.7 |
| TAMSLLWK. + 2y6.light | 475.262 | 777.433 | 65.8 | 22.8 |
| TAMSLLWK. + 2y5.light | 475.262 | 646.392 | 65.8 | 22.8 |
| TAMSLLWK. + 2y3.light | 475.262 | 446.276 | 65.8 | 22.8 |
| TAMSLLWK. + 2y6.heavy | 478.272 | 783.453 | 65.8 | 22.8 |
| TAMSLLWK. + 2y5.heavy | 478.272 | 652.412 | 65.8 | 22.8 |
| TAMSLLWK. + 2y3.heavy | 478.272 | 452.296 | 65.8 | 22.8 |
| SYPLVC[CAM]IAK. + 2y7.light | 525.786 | 800.47 | 69.4 | 25.7 |
| SYPLVC[CAM]IAK. + 2y6.light | 525.786 | 703.417 | 69.4 | 25.7 |
| SYPLVC[CAM]IAK. + 2y5.light | 525.786 | 590.333 | 69.4 | 25.7 |
| SYPLVC[CAM]IAK. + 2y7.heavy | 528.796 | 806.49 | 69.4 | 25.7 |
| SYPLVC[CAM]IAK. + 2y6.heavy | 528.796 | 709.437 | 69.4 | 25.7 |
| SYPLVC[CAM]IAK. + 2y5.heavy | 528.796 | 596.353 | 69.4 | 25.7 |
| ELIPEATEK. + 2y7.light | 515.277 | 787.42 | 68.7 | 25.1 |
| ELIPEATEK. + 2y6.light | 515.277 | 674.336 | 68.7 | 25.1 |
| ELIPEATEK. + 2y3.light | 515.277 | 377.203 | 68.7 | 25.1 |
| ELIPEATEK. + 2y7.heavy | 518.287 | 793.44 | 68.7 | 25.1 |
| ELIPEATEK. + 2y6.heavy | 518.287 | 680.356 | 68.7 | 25.1 |
| ELIPEATEK. + 2y3.heavy | 518.287 | 383.223 | 68.7 | 25.1 |
| FWANFAR. + 2y5.light | 456.23 | 578.305 | 64.4 | 21.7 |
| FWANFAR. + 2y4.light | 456.23 | 507.267 | 64.4 | 21.7 |
| FWANFAR. + 2y1.light | 456.23 | 175.119 | 64.4 | 21.7 |
| FWANFAR. + 2y5.heavy | 461.234 | 583.313 | 64.4 | 21.7 |
| FWANFAR. + 2y4.heavy | 461.234 | 517.276 | 64.4 | 21.7 |
| FWANFAR. + 2y1.heavy | 461.234 | 185.127 | 64.4 | 21.7 |

DP: declustering potential; CE: collision energy.

TABLE 3

Linear regressions of CES1 quantitation calibrators prepared with purified recominant human CES1 proteins at indicated concentrations from 0.59 to 11.82 pmol for six signature peptides

| Signature peptides | Linear regression equations | Coefficient of determination ($R^2$) |
|---|---|---|
| AISESGVALTSVLVK | y = 0.2464x − 0.0059 | 0.9999 |
| FLSLDLQGDPR | y = 0.2948x − 0.0072 | 0.9999 |
| TAMSLLWK | y = 0.2185x − 0.0140 | 1.0000 |
| SYPLVC[CAM]IAK | y = 0.2949x − 0.0400 | 1.0000 |
| ELIPRATEK | y = 0.3443x − 0.0429 | 0.9999 |
| FWANFAR | y = 0.2952x − 0.0391 | 1.0000 |

TABLE 4

Intra-day and inter-day assay precision and accuracy of QC samples of six unique peptides CES1 quantification.

| Nominal CES1 quantities (pmol) | Intra-day (n = 4) | | Inter-day (n = 4) | |
|---|---|---|---|---|
| | Accuracy (%) | Precision (%) | Accuracy (%) | Precision (%) |
| AISESGVALTSVLVK | | | | |
| 1.18 | 101.9 | 2.4 | 96.1 | 5.5 |
| 2.36 | 95.1 | 3.9 | 98.9 | 3.3 |
| 4.73 | 99.2 | 4.5 | 101.4 | 3.1 |
| FLSLDLQGDPR | | | | |
| 1.18 | 100.5 | 2.8 | 97.8 | 1.1 |
| 2.36 | 96.8 | 3.2 | 98.2 | 4.3 |
| 4.73 | 94.7 | 2.6 | 98.2 | 2.3 |
| TAMSLLWK | | | | |
| 1.18 | 106.1 | 2.4 | 100.0 | 9.0 |
| 2.36 | 104.2 | 4.1 | 100.2 | 4.1 |
| 4.73 | 102.3 | 4.0 | 102.2 | 4.4 |
| SYPLVC[CAM]IAK | | | | |
| 1.18 | 97.6 | 4.1 | 98.1 | 5.7 |
| 2.36 | 94.6 | 1.8 | 96.8 | 5.0 |
| 4.73 | 99.1 | 4.8 | 101.5 | 0.8 |
| ELIPEATEK | | | | |
| 1.18 | 95.8 | 4.3 | 98.7 | 6.0 |
| 2.36 | 98.4 | 4.8 | 101.2 | 4.7 |
| 4.73 | 99.6 | 3.3 | 102.2 | 3.2 |
| FWANFAR | | | | |
| 1.18 | 99.4 | 5.5 | 99.7 | 3.2 |
| 2.36 | 100.4 | 2.7 | 100.8 | 3.5 |
| 4.73 | 100.6 | 2.3 | 97.6 | 3.3 |

Having now fully described the disclosure, it will be understood by those of skill in the art that the same can be performed within a wide and equivalent range of conditions, formulations, and other parameters without affecting the scope of the disclosure or any embodiment thereof. All patents, patent applications and publications cited herein are fully incorporated by reference herein in their entirety.

I claim:

1. A method of quantitating protein levels, comprising:
   a) obtaining a cell lysate sample comprising i) a plurality of polypeptides; and ii) a plurality of full-length stable isotope-labeled polypeptides, wherein said full-length isotope polypeptides are obtained by culturing a cell of the same cell type as said cell lysate sample in stable heavy isotope medium;
   b) extracting and digesting said sample to yield a prepared protein fraction;
   c) analyzing said prepared protein fraction with a liquid chromatography-mass spectrometry/mass spectrometry system to obtained mass spectrometry peak areas for said plurality of polypeptides and said full length isotope-labeled polypeptides;
   d) calculating relative peak areas of said plurality of polypeptides and said full length isotope-labeled polypeptides to obtained relative quantitative values; and
   e) comparing the relative peak area ratio of said polypeptides to a standard curve generated using protein quantitation standards to determine the absolute quantity of said plurality of polypeptides.

2. The method of claim 1, wherein said sample is a pool of a plurality of cell lysates from different samples or subjects.

3. The method of claim 1, further comprising the step of determining the identity of said polypeptides.

4. The method of claim 1, wherein said stable heavy isotope medium comprises $^{13}C$ and $^{15}N$.

5. The method of claim 1, wherein said method quantifies as least 2 polypeptides.

6. The method of claim 1, wherein said method quantifies as least 5 polypeptides.

7. The method of claim 1, wherein said method quantifies as least 10 polypeptides.

8. The method of claim 1, wherein said cell lysate is a human cell lysate.

9. The method of claim 1, further comprising the step of performing said method on two different samples and comparing the levels of said polypeptides in each of said two different samples.

10. The method of claim 9, wherein said two different samples comprise a first sample from a healthy subject and a second sample from a subject with a disease.

11. The method of claim 10, wherein said disease is cancer.

12. The method of claim 9, wherein said two different samples comprise a first sample from a subject administered a test compound and second sample from a subject not administered said test compound.

13. The method of claim 1, wherein said sample is from a cell line or subject administered a test compound.

14. The method of claim 13, wherein said test compound is a drug.

15. The method of claim 1, wherein said calculating and comparing is performed using a computer system.

16. The method of claim 15, wherein said computer system comprises a computer processor, computer software, and a display screen.

* * * * *